United States Patent
Farnum

(10) Patent No.: US 10,159,721 B2
(45) Date of Patent: Dec. 25, 2018

(54) ENZYME FORMULATION FOR USE AS FOOD SUPPLEMENT

(71) Applicant: BRYSON PATENTS INC., King City (CA)

(72) Inventor: Bryan Christopher Farnum, King City (CA)

(*) Notice: Subject to any disclaimer, the term of this patent is extended or adjusted under 35 U.S.C. 154(b) by 75 days.

(21) Appl. No.: 14/896,223

(22) PCT Filed: Jun. 26, 2014

(86) PCT No.: PCT/CA2014/000524
§ 371 (c)(1),
(2) Date: Dec. 4, 2015

(87) PCT Pub. No.: WO2015/000053
PCT Pub. Date: Jan. 8, 2015

(65) Prior Publication Data
US 2016/0114012 A1 Apr. 28, 2016

Related U.S. Application Data

(60) Provisional application No. 61/842,774, filed on Jul. 3, 2013.

(51) Int. Cl.
| | |
|---|---|
| *A61K 38/48* | (2006.01) |
| *A61K 38/44* | (2006.01) |
| *A61K 38/47* | (2006.01) |
| *C12N 9/00* | (2006.01) |
| *C12N 9/24* | (2006.01) |
| *C12N 9/58* | (2006.01) |
| *C12N 9/18* | (2006.01) |
| *A61K 38/46* | (2006.01) |
| *A23L 33/10* | (2016.01) |
| *A61K 38/00* | (2006.01) |

(52) U.S. Cl.
CPC .......... *A61K 38/4873* (2013.01); *A23L 33/10* (2016.08); *A61K 38/44* (2013.01); *A61K 38/465* (2013.01); *A61K 38/47* (2013.01); *A61K 38/48* (2013.01); *C12N 9/00* (2013.01); *C12N 9/18* (2013.01); *C12N 9/24* (2013.01); *C12N 9/58* (2013.01); *C12Y 301/01011* (2013.01); *A23V 2002/00* (2013.01); *A61K 38/00* (2013.01); *C12Y 111/01006* (2013.01); *C12Y 301/01* (2013.01); *C12Y 302/01* (2013.01); *C12Y 302/01001* (2013.01); *C12Y 302/01004* (2013.01); *C12Y 302/01022* (2013.01); *C12Y 302/01067* (2013.01); *C12Y 304/00* (2013.01); *C12Y 304/22* (2013.01)

(58) Field of Classification Search
None
See application file for complete search history.

(56) References Cited

U.S. PATENT DOCUMENTS

| | | | | |
|---|---|---|---|---|
| 5,817,350 | A * | 10/1998 | Rhode, Jr. | C12Y 302/01001 424/94.2 |
| 6,451,341 | B1 * | 9/2002 | Slaga | A61K 31/355 424/468 |
| 2008/0199448 | A1 * | 8/2008 | Ross | A61K 31/198 424/94.2 |
| 2008/0213320 | A1 | 9/2008 | Eisenstein et al. | |
| 2013/0156884 | A1 * | 6/2013 | Anderson | A61K 38/48 426/2 |

OTHER PUBLICATIONS

Yor Health, company webpage, description for Yor 1, 2, 3 and 4 products, << https://www.yorhealth.com/downloads/factsPanel/YOR_1234.pdf >>, available online Jun. 2, 2010 as confirmed by Internet Archive Wayback Machine.*

Drugs.com, "Pancron 10 delayed-release capsules" available from company's webpage <<https://www.drugs.com/cdi/pancron-10-delayed-release-capsules.html>> , copyright 2017.*

National Institute of Health, Dietary Supplement Label Database (DSLD), [online] Oct. 1, 2012 (Oct. 1, 2012), [retrieved on Sep. 30, 2014 (Sep. 30, 2014)], Country Life(R)—ZYME-AID(R), Retrieved from the internet: http://www.dsld.nlm.nih.gov/dsld/prdDSF.jsp?db=adsld&id=13485.

National Institute of Health, Dietary Supplement Label Database (DSLD), [online] Apr. 26, 2012 (Apr. 26, 2012), [retrieved on Sep. 30, 2014 (Sep. 30, 2014)], Prosol(TM)—Gastro Calm(TM), Retrieved from the internet: http://www.dsld.nlm.nih.gov/dsld/prdDSF.jsp?db=adsld&id=7792.

National Institute of Health, Dietary Supplement Label Database (DSLD), [online] May 24, 2013 (May 24, 2013), [retrieved on Sep. 30, 2014 (Sep. 30, 2014)], Biotics(R) Research Corporation—Intenzyne Forte(TM), Retrieved from the internet: http://www.dsld.nlm.nih.gov/dsld/prdDSF.jsp?db=adsld&id=13485.

International Search Report of PCT/CA2014/000524; dated Oct. 14, 2014, Marcin Kaminski.

* cited by examiner

*Primary Examiner* — Emily A Cordas
(74) *Attorney, Agent, or Firm* — Benoit & Cote Inc.; Mathieu Miron

(57) ABSTRACT

The present document describes an enzyme formulation comprising an enzyme mixture comprising from about 5% to about 45% (wt/wt) of a fungal protease enzyme; and from about 1.5% to about 50% (wt/wt) of at least one polysaccharide digesting enzyme; in combination with an acceptable pharmaceutical carrier. The present document also describes the use of the formulation of the present invention for the prevention or treatment of digestive disorder.

6 Claims, No Drawings

ENZYME FORMULATION FOR USE AS FOOD SUPPLEMENT

CROSS-REFERENCE TO RELATED APPLICATIONS

This application is a US National Phase application under 35 USC § 371 of PCT/CA2014/000524, filed Jun. 26, 2014, which claims priority from and the benefit of U.S. Patent Application No. 61/842,774, filed on Jul. 3, 2013, the specification of which are hereby incorporated by reference.

BACKGROUND (a) Field

The subject matter disclosed generally relates an enzyme formulation for use as a food supplement. More specifically the enzyme formulation comprises an enzyme mixture of at least one protease enzyme, at least one polysaccharide digesting enzyme, catalase; and lipase.

(b) Related Prior Art

Enzymes are highly specialized biological molecules that serve as catalysts to facilitate reactions in the body that sustain life. Digestive enzymes in particular help to break food down into smaller molecules that can pass from the digestive system into the blood stream for use throughout the body, such as amino acids, glucose, glycerol and fatty acids. They can also help the body to get rid of toxins. The foods eaten by humans also contain enzymes which can help to break down of food. However, cooking food destroys many of these naturally occurring enzymes. Taking supplemental enzymes with food can help us to better digest the food and help to reduce symptoms of digestive distress.

SUMMARY

According to an embodiment, there is provided an enzyme formulation comprising:
an enzyme mixture comprising:
from about 5% to about 45% (wt/wt) of a fungal protease enzyme; and
from about 1.5% to about 50% (wt/wt) of at least one polysaccharide digesting enzyme; and
in combination with an acceptable pharmaceutical carrier.

The fungal protease may be at least one of protease 3.0, protease 4.5, and protease 6.0.

The fungal protease may be protease 3.0, protease 4.5, or protease 6.0.

The polysaccharide digesting enzyme may be at least one of invertase, glucoamylase, lactase, cellulase, alpha-galactosidase, alpha-amylase, and pectinase.

The polysaccharide digesting enzyme may be invertase, glucoamylase, lactase, cellulase, alpha-galactosidase, alpha-amylase, and pectinase.

The enzyme formulation may be further comprising a catalase.

The catalase may be from about 2.5% to 10% (wt/wt) of the formulation.

The enzyme formulation may be further comprising a lipase.

The lipase may be from about 5% to about 15% (wt/wt) of the formulation.

The polysaccharide digesting enzyme, the catalase and the amylase may be from fungal origin.

According to another embodiment, there is provided an enzyme formulation comprising:
an enzyme mixture comprising:
from about 5% to about 45% (wt/wt) of at least one protease enzyme chosen from protease 3.0, protease 4.5, or protease 6.0;
from about 1.5% to about 50% (wt/wt) of at least one polysaccharide digesting enzyme chosen from invertase, glucoamylase, lactase, cellulase, alpha-galactosidase, alpha-amylase, or pectinase;
from about 2.5% to 10% (wt/wt) catalase; and
from about 5% to about 15% (wt/wt) lipase,
in combination with an acceptable pharmaceutical carrier.

According to another embodiment, there is provided a food supplement comprising an enzyme formulation of the present invention.

According to another embodiment, there is provided a use of an enzyme formulation of the present invention for preventing or treating a digestive disorder.

The digestive disorder may comprise dyspepsia, abdominal pain, lactose intolerance, gastroesophageal reflux, inflammatory bowel disease, and constipation.

The dyspepsia comprises at least one of bloating, belching, nausea, and heartburn.

According to another embodiment, there is provided a method for preventing or treating a digestive disorder comprising administering to a subject in need thereof an effective amount of a composition of the present invention.

The digestive disorder may comprise dyspepsia, abdominal pain, lactose intolerance, gastroesophageal reflux, inflammatory bowel disease, and constipation.

The dyspepsia may comprise at least one of bloating, belching, nausea, and heartburn.

The following terms are defined below.

The term "fungal origin" is intended to mean that the enzymes used in the compositions of the present invention have been isolated from isolated fungal strains, such as for example *Aspergillus oryzae* and *Aspergillus niger*.

The term "pharmaceutically acceptable carrier" is intended to mean that the carrier may take a wide variety of forms depending on the form of preparation desired for administration, e.g., oral, mucosal (eg., nasal, sublingual, vaginal, cystic, rectal, ocular, buccal or aural), parenteral (including intravenous, subcutaneous, bolus injection, intramuscular or intraarterial) or topical (eg., transdermal, transcutaneous, eye drops or other ophthalmic preparations). Thus, the compositions of the present invention can be presented as discrete units suitable for oral administration such as capsules (coated or non-coated with polymers as sustained release or enteric coated), sachets or tablets (coated or uncoated or bilayers) each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion, liposomes, nanosuspension, as may be required by the desired formulation. In addition to the common dosage forms set out above, the active ingredients may also be administered by controlled or modified release formulation and/or delivery devices. The compositions may be prepared by any of the methods of pharmacy. In general, such methods include a step of bringing into association the active ingredient with the excipients or carriers that constitutes one or more necessary ingredients. In general, the compositions are prepared by uniformly and intimately admixing the active ingredient with liquid carriers/excipients or finely divided solid carriers/excipients or both. The product can then be conveniently shaped into the desired presentation.

Thus, the pharmaceutical compositions of this invention may include pharmaceutically acceptable carrier/excipients and active ingredients.

The pharmaceutical carrier employed can be, for example, to form oral solid preparations such as powders, capsules and tablets include fillers such as talc, calcium carbonate, microcrystalline cellulose, kaolin, mannitol, silicic acid, sorbitol, starch, and mixture thereof. Disintegrants such as croscarmellose sodium, crospovidone, sodium starch glycolate, pre-gelatinized starch, gums and other starches and mixtures thereof. Lubricants such as calcium stearate, magnesium stearate, syloid silica gel, mineral oil, glycerine, sorbitol, mannitol, polyethylene glycol, stearic acid, sodium lauryl sulphate, talc, hydrogenated vegetable oil (eg., peanut oil, sesame oil, corn oil or soybean oil), ethyl oleate agar and mixtures thereof. Because of their ease of administration, tablets and capsules are the preferred oral dosage units whereby solid pharmaceutical carriers are employed. Each of the solid oral dosage units can be further coated with specialized polymers that can delay release or sustained release the contents of the dosage units. The active ingredients can be administered by delayed release or sustained release means or by delivery devices that are well known to those of ordinary skill in the art. Non-limiting examples of delayed release or sustaine release include those described in U.S. Pat. Nos. 3,845,770; 3,916,899; 3,536,809; 5,059,595. Such dosage forms can be used to provide slow or controlled release of one or more ingredients using for example polymers such as hydropropylmethyl cellulose usually in a matrix form such as gel, permeable membranes, osmotic systems, liposomes, microspheres or combinations thereof. Controlled release formulation can be used to protect the dosage units from exposure to the gastric environment; delay release of active ingredients to the lower gastrointestinal tract such as the colon; or slow the release of the active ingredient such that blood levels of the drug can be lowered and affect the occurrence of side effects.

In preparing the oral liquid compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions.

A tablet containing the composition of this invention may be prepared by compression or molding, optionally with one or more accessory ingredients or adjuvants.

Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.001 mg to about 5000 mg of the active ingredients and each cachet or capsule preferably containing from about 0.001 mg to about 5000 mg of the active ingredient.

The pharmaceutical compositions must be stable under the conditions of manufacture and storage; thus, preferably should be preserved against the contaminating action of microorganisms such as bacteria and fungi such as benzalkonium chloride, chlorobutanol, methyl paraben, propyl paraben, edetate disodium, sorbic acid or other agents known to those skilled in the art.

Pharmaceutical compositions of this invention can be in a form suitable for rectal administration wherein the carrier is a solid or liquid or spray. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing the active ingredients of the present invention, may also be prepared in powder or liquid concentrate form. Addition of preservatives such as anti-oxidants are widely acceptable in pharmaceutical arts as a means of simulating long-term storage in order to determine characteristics such as shelf life or stability of formulations over time (See eg., Jens T. Carstensen, Drug stability: Principles & Practice. 2nd Ed., Marcel Dekker, NY, N.Y. 1995, pp 379-80).

The term "digestive disorder" is intended to mean disorders associated with the digestive function, which are mostly associated with symptoms including bloating, diarrhea, gas, stomach pain, and stomach cramps, and which may be treated, usually, with medication and lifestyle changes.

The term "dyspepsia" is intended to mean "indigestion", a condition of impaired digestion. It is characterized by chronic or recurrent pain in the upper abdomen, upper abdominal fullness and feeling full earlier than expected when eating. It can be accompanied by bloating, belching, nausea, or heartburn. Dyspepsia is a common problem and is frequently caused by gastroesophageal reflux disease (GERD) or gastritis. This includes functional dyspepsia (previously called nonulcer dyspepsia is dyspepsia "without evidence of an organic disease that is likely to explain the symptoms". Functional dyspepsia is estimated to affect about 15% of the general population in Western countries.

The term "abdominal pain" is intended to mean pain associated with the abdomen including mild stomach ache, sharp pain, or stomach crampsor the likes. In the context of the present invention, such pain is most likely associated with digestive disorders such as indigestion (aka dyspepsia), constipation, food poisoning, food allergies, gas, lactose intolerance, and gastroesophageal reflux.

The term "lactose intolerance" is intended to mean lactase deficiency and hypolactasia, which is the inability to digest lactose, a sugar found in milk and to a lesser extent dairy products. As a genetic disorder, it prevents babies from drinking human milk. Lactose intolerant individuals have insufficient levels of lactase, an enzyme that catalyzes hydrolysis of lactose into glucose and galactose, in their digestive system. In most cases this causes symptoms which may include abdominal bloating and cramps, flatulence, diarrhea, nausea, borborygmi (rumbling stomach), or vomiting after consuming significant amounts of lactose. Some studies have produced evidence that milk consumption by lactose intolerant individuals may be a significant cause of inflammatory bowel disease.

The term "gastric reflux" is intended to mean the major symptom of reflux of gastric fluid which is commonly associated with gastroesophageal reflux disease (GERD), heartburn, which may include abnormal relaxation of the lower esophageal sphincter, which normally holds the top of the stomach closed, impaired expulsion of gastric reflux from the esophagus, or a hiatal hernia. These changes may be permanent or temporary.

The term "constipation" (also known as costiveness or dyschezia) is intended to mean bowel movements that are infrequent or hard to pass. Constipation is a common cause of painful defecation. Severe constipation includes obstipation (failure to pass stools or gas) and fecal impaction, which can progress to bowel obstruction and become life-threatening. Constipation is a symptom with many causes. These causes are of two types: obstructed defecation and colonic slow transit (or hypomobility). About 50% of patients evaluated for constipation at tertiary referral hospitals have obstructed defecation. This type of constipation has mechanical and functional causes. Causes of colonic slow transit constipation include diet, hormonal disorders such as hypothyroidism, side effects of medications, and rarely heavy metal toxicity. Constipation is common; in the general population incidence of constipation varies from 2 to 30%.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION

In embodiments there is disclosed an enzyme formulation comprising:
  an enzyme mixture comprising:
    from about 5% to about 45% (wt/wt) of a fungal protease enzyme;
    from about 1.5% to about 50% (wt/wt) of at least one polysaccharide digesting enzyme; and
  in combination with an acceptable pharmaceutical carrier.

According to an embodiment the enzyme formulation of the present invention is a food supplement that may improve digestion of nutrients. The formulation also helps reducing heartburn, gas and bloating caused by difficulty in digestion. It may also improve medical conditions such as inflammatory bowel disease, lactose intolerance, and other intestinal ailments.

Proteases

A protease (also termed peptidase or proteinase) is any enzyme that conducts proteolysis, that is, begins protein catabolism by hydrolysis of the peptide bonds that link amino acids together in the polypeptide chain forming the protein. Proteases are a type of enzyme that functions mainly to help digest different kinds of proteins. These enzymes break down the bonds by a process known as hydrolysis and convert proteins into smaller chains (peptides), or into even smaller units (amino acids). Proteins have a complex folded structure requiring these types of enzymes to disassemble the molecule in very specific ways. Without proteases the intestinal lining would not be able to digest proteins, causing serious consequences to your health.

According to an embodiment, the protease or proteases may represent from about 5% to about 45%, or from about 5% to about 40%, or from about 5% to about 35%, or from about 5% to about 30%, or from about 5% to about 25%, or from about 5% to about 20%, or from about 5% to about 15%, or from about 5% to about 10%, or from about 10% to about 45%, or from about 15% to about 45%, or from about 20% to about 45%, or from about 25% to about 45%, or from about 30% to about 45%, or from about 35% to about 45%, or from about 40% to about 45%, or from about 5% to about 40%, or from about 10% to about 40%, or from about 15% to about 40%, or from about 20% to about 40%, or from about 25% to about 40%, or from about 30% to about 40%, or from about 35% to about 40%, or from about 5% to about 35%, or from about 10% to about 35%, or from about 15% to about 35%, or from about 20% to about 35%, or from about 25% to about 35%, or from about 30% to about 35%, or from about 5% to about 30%, or from about 10% to about 30%, or from about 15% to about 30%, or from about 20% to about 30%, or from about 25% to about 30%, or from about 5% to about 25%, or from about 10% to about 25%, or from about 15% to about 25%, or from about 20% to about 25%, or from about 5% to about 20%, or from about 10% to about 20%, or from about 15% to about 20%, or from about 5% to about 15%, or from about 10% to about 15%, or from about 5% to about 10% (wt/wt) of the formulation. Preferably, the protease comprises protease 3.0, protease 4.5, and protease 6.0.

The Health Benefits of Protease. Proteolytic enzymes are extremely important for the digestion of many foods. They also digest the cell walls of unwanted harmful organisms in the body and break down unwanted wastes such as toxins, cellular debris, and undigested proteins. In this way, protease helps digest the small stuff, so that our immune system can work hard to avoid toxin overload.

With the distinct ability to breakdown peptide bonds and liberate amino acids, proteolytic enzymes are now being studied by modern science and medicine for their clinical and therapeutic use in the realms of general oncology, inflammatory issues, and overall immune function. They are thought to be involved in a large number of processes and/or processes such as inflammatory bowel disease, repair of skin burns and stomach ulcers, sprains and pain relief, slow or stopping of inflammation, osteoarthritic pain, sports-related injuries, beneficial to gut bacteria, circulatory and lymph system, clotting, digestive diseases.

Protease 6.0

The pH varies throughout the digestive system, from a pH of 6.8 in the mouth, to as low as 1.0 to 2.0 in the stomach, to a pH of 8.5 in the small intestine. Protease 6.0 (also called Alkaline Protease) is a mixture of acid, neutral and alkaline proteases that demonstrates both exo-peptidase and endo-peptidase activity with high substrate specificity. Protease 6.0 has an effective pH range from 2.75 to 7.0. The USP protease activity occurs at an alkaline pH and works synergistically with endogenous protease to digest protein in the small intestine. For this reason, protease 6.0 (Alkaline Protease) works synergistically with endogenous enzymes to provide protein digestion through all portions of the digestive tract.

According to an embodiment, the sources of the enzyme may be: *Aspergillus oryzae* and *Aspergillus niger*, and preferably *Aspergillus niger* and it may be used as a digestive aid. Dosage should not to exceed 680000 HUT per day day (both Protease 4.5 and 6.0 are measured in HUT (Hemoglobin Unit Tyrosine base)), and include quantities in both mg and enzymatic activity units. For multi-ingredient products containing protease from *A. niger* and from *A. orzyae* the maximum dosage from both sources cannot exceed 680000 HUT and 6800 SAP per day.

Protease 4.5

Protease 4.5 (Acid Protease) is a mixture of acid, neutral, and alkaline proteases that demonstrate both exo-peptidase and endo-peptidase activity with high substrate specificity. Protease 4.5 (Acid Protease) has an effective pH range of 2.75 to 6.25. For this reason, Protease 4.5 (Acid Protease)

works synergistically with endogenous enzymes to provide protein digestion in the stomach and superior duodenal region of the small intestine.

According to an embodiment, the sources of the enzyme may be: *Aspergillus oryzae* and *Aspergillus niger*, and preferably *Aspergillus niger* and it may be used as a digestive aid. Dosage should not to exceed 680000 HUT per day day (both Protease 4.5 and 6.0 are measured in HUT (Hemoglobin Unit Tyrosine base)), and include quantities in both mg and enzymatic activity units. For multi-ingredient products containing protease from *A. niger* and from *A. orzyae* the maximum dosage from both sources cannot exceed 680000 HUT and 6800 SAP per day.

Protease 3.0

Protease 3.0 is characterized by its ability to hydrolyze proteins under acid conditions. The broad specificity of acid-stable protease enables the enzyme to, easily and efficiently, hydrolyze most soluble proteins. Because protease 3.0 has an effective pH range of 2.75 to 4.7, it is uniquely suited to work synergistically with endogenous pepsin to provide protein digestion in the stomach.

According to an embodiment, the sources of the enzyme are: *Aspergillus oryzae* and *Aspergillus niger*, and preferably *Aspergillus niger* and it may be used as a digestive aid. Dosage should not to exceed 6,800 SAPU per day day (both Protease 4.5 and 6.0 are measured in HUT (Hemoglobin Unit Tyrosine base)), and include quantities in both mg and enzymatic activity units. For multi-ingredient products containing protease from *A. niger* and from *A. orzyae* the maximum dosage from both sources cannot exceed 680000 HUT and 6800 SAP per day.

Polysaccharide Digesting Enzyme

Polysaccharides are long carbohydrate molecules of monosaccharide units joined together by glycosidic bonds. They range in structure from linear to highly branched. Polysaccharides are often quite heterogeneous, containing slight modifications of the repeating unit. Depending on the structure, these macromolecules can have distinct properties from their monosaccharide building blocks. Polysaccharide digesting enzymes are proteins that catalyze the digestion of these polysaccharides by hydrolysis.

According to an embodiment, the polysaccharide digesting enzyme may represent from about 1.5% to about 50%, or from about 1.5% to about 45%, or from about 1.5% to about 40%, or from about 1.5% to about 35%, or from about 1.5% to about 30%, or from about 1.5% to about 25%, or from about 1.5% to about 20%, or from about 1.5% to about 15%, or from about 1.5% to about 10%, or from about 1.5% to about 5%, or from about 1.5% to about 2.5%, or from about 1.5% to about 2%, or from about 2% to about 50%, or from about 2% to about 45%, or from about 2% to about 40%, or from about 2% to about 35%, or from about 2% to about 30%, or from about 2% to about 25%, or from about 2% to about 20%, or from about 2% to about 15%, or from about 2% to about 10%, or from about 2% to about 5%, or from about 2% to about 2.5%, or from about 2.5% to about 50%, or from about 2.5% to about 45%, or from about 2.5% to about 40%, or from about 2.5% to about 35%, or from about 2.5% to about 30%, or from about 2.5% to about 25%, or from about 2.5% to about 20%, or from about 2.5% to about 15%, or from about 2.5% to about 10%, or from about 2.5% to about 5%, or from about 5% to about 50%, or from about 5% to about 45%, or from about 5% to about 40%, or from about 5% to about 35%, or from about 5% to about 30%, or from about 5% to about 25%, or from about 5% to about 20%, or from about 5% to about 15%, or from about 5% to about 10%, or from about 10% to about 50%, or from about 10% to about 45%, or from about 10% to about 40%, or from about 10% to about 35%, or from about 10% to about 30%, or from about 10% to about 25%, or from about 10% to about 20%, or from about 10% to about 15%, or from about 15% to about 50%, or from about 15% to about 45%, or from about 15% to about 40%, or from about 15% to about 35%, or from about 15% to about 30%, or from about 15% to about 25%, or from about 15% to about 20%, or from about 20% to about 50%, or from about 20% to about 45%, or from about 20% to about 40%, or from about 20% to about 35%, or from about 20% to about 30%, or from about 20% to about 25%, or from about 25% to about 50%, or from about 25% to about 45%, or from about 25% to about 40%, or from about 25% to about 35%, or from about 25% to about 30%, or from about 30% to about 50%, or from about 30% to about 45%, or from about 25% to about 40%, or from about 25% to about 35%, or from about 25% to about 30%, or from about 35% to about 50%, or from about 35% to about 45%, or from about 35% to about 40%, or from about 40% to about 50%, or from about 40% to about 45%, or from about 45% to about 50% (wt/wt) of the formulation. Preferably, the protease comprises invertase, glucoamylase, lactase, cellulase, alpha-galactosidase, alpha-amylase, and pectinase.

Invertase

Invertase is the enzyme that breaks down table sugar into fructose and glucose. It is commonly used in candy making, to make the inside of a candy liquid. Taken as a digestive enzyme, it enhances the overall digestion of starch, sugar and other carbohydrates.

Invertase is one of the essential enzymes nature uses to help us digest sugars. Commonly found in bee pollen and yeast sources, invertase plays a key role not only in digestive processes, but also, and perhaps more importantly, in overall human disease prevention, physical rejuvenation and anti-ageing processes. As we age, we have less access to this natural enzyme, resulting in a reduced ability to extract the vital nutrients from the food we eat. It can also slow our digestive process, as sugars and starches are such a big part of most American diets. And, while some forms of sugar and carbohydrates are good for the body, they cannot be absorbed or digested well without the help of the invertase enzyme. In contrast to many other enzymes, invertase has the distinct ability to remain active within a wide range of pH levels.

Invertase is thought to provide several health related benefits, such as acting as a natural immune booster, antioxidant properties, powerful anti-microbial activity, ulcers prevention as well as many other digestive diseases, natural antibacterial and antiseptic, reduction of colds, flu and other respiratory infections, cancer therapy support.

Glucoamylase

Glucoamylase (also known as amyloglucosidase) is a type of digestive enzyme that cleaves or breaks off a free glucose molecule from the complex sugar-based chains that form starch or from the simpler sugar, maltose. The glucose that is freed can then be used as a source of energy for the body.

Glucoamylase helps to break down starch that occurs naturally in most vegetables that we eat (in very high amounts in common foods like potatoes, corn, rice, and wheat) or is added as filler or processing additive in many prepared food products. It is a specific type of amylase (starch-digesting enzyme) that our bodies produce in the mouth and pancreas, but it may also be derived from non-animal sources.

Glucoamylase is often described separately from amylase because it digests starches in a particular way, removing free glucose molecules from the end of the starchy chains rather than simply breaking these longer chains simply into smaller chains. It is part of an extremely important group of enzymes that allow us to absorb nutrients and create energy from some of the most common plant foods that we eat.

The Health Benefits of Glucoamylase: Every day, human beings eat large amounts of starches, and while these carbohydrates have some nutritional value, they cannot be absorbed or digested by the body without the help of enzymes. Glucoamylase is one type of enzyme that can break down these starches into glucose, which is absorbable and usable. This helps take the heavy load off of our digestive processes, reducing many common digestive upsets such as heaviness, lethargy, bloating, gas and loose stools. Here are some of the health benefits of glucoamylase: reduce irritable bowel syndrome, reduce digestive upsets and gastrointestinal issues, autoimmune diseases and inflammation, reduce load on digestive organs, balance blood sugar, and reduce food allergies.

According to an embodiment, glucoamylase is isolated from *Aspergillus niger, Aspergillus oryzae, Rhizopus niveus, Rhizopus oryzae*; preferable from *Aspergillus niger*). It is used as a digestive enzyme in a dosage which should not to exceed 300 AGU per day.

Lactase

Lactase is an enzyme that hydrolyzes milk sugar (lactose) into its component parts, glucose and galactose, and assists in the digestion of dairy products such as ice cream, milk and cheese. Nutritionists estimate that 10-20% of the U.S. population is lactose intolerant, meaning they have an inability to break down lactose in many of the dairy products they eat.

Some ethnic groups have much higher levels of lactose intolerance. For example, research suggests that up to 75% of all African-Americans and Native Americans, and 90% of Asian-Americans experience at least some difficulty digesting milk sugar.

The body naturally produces the lactase enzyme in the brush border of our small intestines, unless we are lactose intolerant. The use of lactase as a supplemental agent to help people properly digest lactose has long been confirmed by the scientific community. Here are some of the great health benefits and studies that support the benefits of enzymes such as lactase: lactose intolerance, reduces gas and bloating, irritable bowel syndrome, digestive upset in children with autism, inflammation of the digestive tract, prevention of certain digestive issues (chronic diarrhea, cramping and abdominal distension).

According to an embodiment, the sources of lactase may be from *Aspergillus flavus* var. *oryzae*. The enzyme is used as a digestive enzyme, to assist in the digestion of foods containing lactose, and help prevent symptoms of lactose intolerance (including gas, bloating, cramping and diarrhea). According to another embodiment, the dosage may be: as digestive enzyme/aid: Not to exceed 18,000 ALU 1-3 times per day; as lactose digestion: Not to exceed 3,000 to 18,000 ALU 1-3 times per day.

Cellulase

Cellulase helps to break down cellulose, the major component in the fibrous complex which surrounds each plant's cell walls, called cellulose. Cellulose is a carbohydrate and a key part of the outer cellular structure of vascular plants. It could be considered one of the most abundant compounds in the world, as it is the basic building block for much of the plant kingdom, and is a primary food for much of the world's living organisms.

Humans do not manufacture cellulase which is needed to digest this type of fiber and so, must rely on fermentation by the flora in the large intestine. This process allows us to break down a small portion of these plant fibers, but the rest act as bulking agents that are eliminated in the stool. If lots of juicy, healthy greens, sprouts and herbs, are eaten, one need to make sure that they can be digested, or at least increase their digestion by having enough cellulase available.

Cellulase breaks down cellulose into beta-glucose. Glucose, or blood sugar, is the body's key source of energy. It can be a problem, though, when simple sugars that quickly elevate our blood sugar levels are eaten because the excess is converted into triglycerides and stored as body fat. Glucose from cellulose is released slowly and should not dramatically increase blood sugar but rather provide a more stable fuel for the body. In addition, the fiber that is not digested by the cellulase can also slow down or decrease the absorption of fats including cholesterol.

Cellulase enzymes may aid in the hydrolysis of cellulose into energy-sustaining blood sugar that may help maintain optimal blood sugar levels, in keeping cholesterol in the blood stream at optimal levels, supporting cell membranes to keep them healthy from free radicals, toxic chemicals, and other entities that are harmful to cell membranes, aid in mediation of biofilm formation from cellulose produced by many types of pathogens, breaking down the polysaccharides of microbial biofilms.

In vitro studies show that the cellulase enzymes can stop the growth and increase the breakdown of biofilms produced by the bacteria Pseudomonas. This helps detoxify the intestinal tract, as well as the body's major organ systems.

One study of nursing home patients taking a multi-enzyme formula containing cellulase found that they favorably increased markers of protein absorption. This indicates an improvement in digestion of a nutritional formula also given to the study participants, which would lead to an overall better nutritional status. Other tests also indicated an improvement in immune function for the patients. What is more, when the enzyme supplement was withdrawn, the positive benefits ended.

According to an embodiment, the sources of the cellulose may be *Aspergillus niger, Trichoderma longbrachiatum, Trichoderma reesei*. Preferably, the enzyme is from *Trichoderma longbrachiatum*. According to an embodiment, it is used as a digestive enzyme. Dosage should not exceed 110,000 CU per day, and should be taken with food/meal.

Alpha-galactosidase

Beans, greens (especially cruciferous vegetables like broccoli, cabbage and cauliflower) and heavy carbohydrate-laden foods can cause gassiness and bloating. These foods have carbohydrates that are linked to proteins or fats (known as glycoproteins or glycolipids) which aren't effectively broken down in the gut; these poorly-digested particles then serve as a food source for intestinal bacteria. These bacteria ferment the leftovers producing hydrogen and carbon dioxide gas as byproducts. Excess gas is the culprit for most of the discomfort we feel when eating these foods. One enzyme that halts this process is alpha galactosidase.

The extent to which humans can break down starchy, hard-to-digest foods is relatively dependent upon the amount of alpha-galactosidase present. The human body produces this enzyme in the mouth in the saliva, as well as in the pancreas, from which it moves into the small intestine and the rest of the digestive tract. With age, the body produces less of this enzyme. If not enough enzyme is produced because of age, genetics, or for any other reason, this greatly increase our chances of having undigested or partially-digested food particles in our digestive tracts that can stimulate the growth of bacteria, leading to indigestion, causing abdominal cramps, gas, and help develop an environment that foster overgrowth of *Candida* and yeast infections.

Alpha-galactosidase is a glycoprotein that hydrolyzes molecules from glycolipids and glycoproteins found in complex sugars. On a cellular level, alpha-galactosidase causes an important reaction in the cellular lysosome, an organelle inside our cells that is crucial in the breakdown of multiple types of biomolecules. In other words, is helps us break down the polysaccharides and oligosaccharides found in foods that are typically more-challenging to digest such as peanuts, beans, lentils and cruciferous vegetables, such as cauliflower, cabbage, broccoli and Brussels sprouts.

The health benefits of alpha-galactosidase: aids in digestion of complex sugar and fat, reduces intestinal gas, reduces complex carbohydrate intolerance, help with Fabry's disease.

Studies show that people without enough alpha-galactosidase can experience a very serious condition known as Fabry's disease, which can later lead to kidney malfunction and an increased risk of heart disease. A genetic condition, Fabry disease causes abnormal deposits of fatty substances to accumulate in blood vessel walls, due to the inherited lack of alpha galactosidase. Currently, the U.S. government is sponsoring clinical trials to study more about how alpha-galactosidase can prevent or treat this serious condition.

According to an embodiment, the sources of the enzyme may be from *Aspergillus niger*. According to another embodiment it may be used as a digestive enzyme, to helps reduce gas production/flatulence following a meal rich in fermentable carbohydrates (such as vegetables, pulses/legumes/beans and whole grains), helps prevent gastrointestinal intolerance of oligosaccharides/fermentable carbohydrates. The dosage for digestive enzyme; reduce gas production: Not to exceed 3,000 GalU per day; to prevent gastrointestinal intolerance: Not to exceed 260 to 3,000 GalU per day and it should be taken with first bite of food/meal.

Alpha-amylase

Amylase is one of the primary starch-digesting enzymes secreted in the body. It is somewhat unusual in that it is produced not only by the pancreas but also in the mouth as a component of saliva. This form is known as ptyalin, and it begins the enzymatic digestion of starches in the oral cavity as food is chewed and mixed with saliva. This begins the reduction of larger, more complex starches into simpler sugars; however the process is largely arrested as the food enters the more acidic environment of the stomach.

Pancreatic amylase goes into action after the partially digested food is emptied into the small intestine and the pH returns to the neutral range. Starches continue to be broken into smaller trisaccharides and disaccharides and possibly even into glucose for energy. The primary type of amylase is known as alpha amylase, which hydrolyses (breaks down) the bonds in long starch or glycogen molecules into smaller chains of glucose called dextrins, which are easier to digest. Amylase is also produced by various bacteria and fungal organisms like *Aspergillus oryzae* from which it can be isolated for effective, vegan-safe dietary supplements.

One of the most important parts of the digestive process occurs in the mouth and the saliva. The enzyme amylase helps to relieve the burden of digestion on the small intestine by breaking down food particles while still in the mouth. If this important enzyme were not excreted in the saliva, the small intestine would have a much harder time breaking down sugars and starches. In this way, amylase helps the entire functioning of the digestive system.

Due to poor dietary habits and age most people become deficient in amylase production and may show some signs of deficiency which may include skin rash, allergies, gas, constipation, mood imbalances and general digestive upset. What is more, having sufficient amylase activity reduces inflammation (one of the primary causes for so many degenerative diseases), as it helps the body digests and excrete inflammation-response dead white blood cells. Without proper amylase activity, inflammation can be excessive. Low amylase is also thought to be a factor in a variety of diseases including type II diabetes, blood sugar imbalances, hypoglycemia, carbohydrate and sugar cravings, and many forms of food sensitivities.

The health benefits of amylase are thought to be to help lower autoimmune and inflammation responses, resistance to inflammation, compromised health support, lessen the aging effects, According to an embodiment, the sources of the enzyme may be *Aspergillus flavus* var. *oryzae, Aspergillus niger, Hordeum vulgare* (seed), and *Rhizopus oryzae*. The enzyme may be used as a digestive enzyme, and the dosage should not exceed 150000 FCC alpha-amylase dextrinizing units (DU) per day, not to exceed 34000 DU per single dose, and the enzyme should be taken with food/meal.

Pectinase

Commonly found in many fruits such as bananas and apples, pectinase plays a key role not only in the digestive processes, but also, and perhaps more importantly, in total physical well-being and anti-aging.

Pectin is a type of fiber that makes up the cell wall of many types of fruits and vegetables. It is composed of long polysaccharides that form a gelatinous substance in the center of the plant cell wall and between plant cells. It occurs primarily in the non-woody parts of plants, which, of course, are the parts that most likely to be consumed.

Pectin is a part of our diet not only because of its presence in the fruits and vegetable, but it is also used extensively as a gelling and thickening agent in processed foods, particularly as a thickener in jams and jellies. Pectinase, along with cellulase and hemicellulase, helps with the digestion of plant-based foods, increasing their nutritional and prebiotic value.

During the ripening process plants generally use pectinase to hydrolyze (break down) some of the pectin in and between the cell walls making the cell walls weaker, and therefore soft and edible. This means that when you test an apple or tomato at the grocery store or, even better, before plucking it out of the garden, you are actually checking in part to see if pectinase has become more active indicating that the fruit is ripe and ready to eat.

The health benefits that are thought to be brought about by pectinase are the promotion, growth and health of intestinal microbiota, provides fuel for colon lining, increase digestibility and absorption of plant-foods;

According to an embodiment, the sources of the enzyme may be *Aspergillus niger, aspergillus oryzae, Trichoderma longibrachiatum, Trichoderma reesei*. It is to be used as a digestive enzyme. Dosage is not to exceed 180 Endo-PG per day, taken with food/meal.

Other Enzymes

Lipase

Lipase is a very important enzyme in the process of digesting fatty substances (lipids) that can be found in the human metabolism, or as part of a diet. It hydrolyzes fats into its single fatty acid and glycerol molecules, so the intestines can absorb them.

Cells use lipids (fats) to create their structure and protection. So, just as we must concern ourselves with getting proper amounts of healthy fats, we must also make sure that we have the good pancreatic enzymes that can absorb this fat along with many fat-soluble nutrients including vitamins A, D, E, and K. This is the role of lipase. Without this enzyme, we are left with some of the typical types of digestive upset such as indigestion and heartburn.

Lipase not only helps us break down fat, preventing excess weight gain and possibly even obesity, but it also has the ability to streamline the entire digestion process and increase the nutritional value of the natural fats we are getting from good, healthy foods. This is particularly important in light of the fact that many people consume less-than-optimal amounts of essential fatty acids and fat-soluble nutrients, meaning that it is more important than ever to digest and absorb these as efficiently as possible. In addition, the common effects of indigestion, bloating, abdominal discomfort and gas resulting from eating high-fat foods can be greatly alleviated.

The Health Benefits of Lipase: Lipase is thought to help keep pancreatic enzymes at optimal levels as we age, improve symptoms of Celiac disease, improve common symptoms of indigestion, improve overall nutritional status for those with cystic fibrosis, helps boost immune function, boosts absorption of vitamins and minerals from food, aid in fat digestion and weight control.

According to an embodiment, the sources of lipase may be from *Aspergillus flavus* var. *oryzae, Aspergillus niger, Rhizopus oryzae* and preferable from *Aspergillus niger*. The lipase is used as a digestive enzyme, and dosages in adults should not to exceed 110,000 FCCLU per day, not to exceed 30,000 FCCLU per dose.

According to an embodiment, the lipase may represent from about 5% to about 15%, or from about 5% to about 14%, or from about 5% to about 13%, or from about 5% to about 12%, or from about 5% to about 11%, or from about 5% to about 10%, or from about 5% to about 9%, or from about 5% to about 8%, or from about 5% to about 7%, or from about 5% to about 6%, 6% to about 15%, or from about 6% to about 14%, or from about 6% to about 13%, or from about 6% to about 12%, or from about 6% to about 11%, or from about 6% to about 10%, or from about 6% to about 9%, or from about 6% to about 8%, or from about 6% to about 7%, 7% to about 15%, or from about 7% to about 14%, or from about 7% to about 13%, or from about 7% to about 12%, or from about 7% to about 11%, or from about 7% to about 10%, or from about 7% to about 9%, or from about 7% to about 8%, 8% to about 15%, or from about 8% to about 14%, or from about 8% to about 13%, or from about 8% to about 12%, or from about 8% to about 11%, or from about 8% to about 10%, or from about 8% to about 9%, 9% to about 15%, or from about 9% to about 14%, or from about 9% to about 13%, or from about 9% to about 12%, or from about 9% to about 11%, or from about 9% to about 10%, 10% to about 15%, or from about 10% to about 14%, or from about 10% to about 13%, or from about 10% to about 12%, or from about 10% to about 11%, 11% to about 15%, or from about 11% to about 14%, or from about 11% to about 13%, or from about 11% to about 12%, 12% to about 15%, or from about 12% to about 14%, or from about 12% to about 13%, 13% to about 15%, or from about 13% to about 14%, 14% to about 15% (w/w) of the enzyme formulation.

Catalase

The catalase enzyme is so critical to our health that it is found in nearly every living organism on the planet that is exposed to oxygen. This antioxidant enzyme can catalyze the conversion of hydrogen peroxide into water and oxygen. Hydrogen peroxide is a by-product of cell metabolism, which serves some useful functions including healthy immune response.

Catalase has one of the highest rates of turnover when compared to all other enzymes. One catalase enzyme can change 40 million molecules of hydrogen peroxide into water and oxygen in just one second. Catalase enzymes act to protect our cells, counteracting and balancing the continual production of hydrogen peroxide.

Because of its undeniable, scientifically-proven powerful antioxidant properties, catalase is very beneficial to the organs and body processes. In addition to acting as a super antioxidant, catalase also has the ability to use hydrogen peroxide to oxidize toxins including methanol, ethanol, formic acid, formaldehyde, and nitrite. This type of dual activity makes it a crucial cellular enzyme.

The Health Benefits of catalase are as a powerful antioxidant support, possible anti-aging and anti-degenerative effects (increase lifespan), fat reduction in organ fat in lab rats, and prevention of DNA damage.

According to an embodiment, the sources of the enzyme may be *Aspergillus niger, Saccharomyces cerevisiae*. Preferably, the enzyme is from *Aspergillus niger*. According to an embodiment, the enzyme is used as a digestive enzyme. The dosage should exceed 3200 Baker units per day (approx. 180000 CatU per day, and it should be taken with food/meal.

According to an embodiment, the catalase may represent from about 2.5% to about 10%, or from about 2.5 to about 9%, or from about 2.5 to about 8%, or from about 2.5 to about 7%, or from about 2.5 to about 6%, or from about 2.5 to about 5%, or from about 2.5 to about 4%, or from about 2.5 to about 3%, or from about 3% to about 10%, or from about 3% to about 9%, or from about 3% to about 8%, or from about 3% to about 7%, or from about 3% to about 6%, or from about 3% to about 5%, or from about 3% to about 4%, or from about 4% to about 10%, or from about 4% to about 9%, or from about 4% to about 8%, or from about 4% to about 7%, or from about 4% to about 6%, or from about 4% to about 5%, or from about 5% to about 10%, or from about 5% to about 9%, or from about 5% to about 8%, or from about 5% to about 7%, or from about 5% to about 6%, or from about 6% to about 10%, or from about 6% to about 9%, or from about 6% to about 8%, or from about 6% to about 7%, or from about 7% to about 10%, or from about 7% to about 9%, or from about 7% to about 8%, or from about 8% to about 10%, or from about 8% to about 9%, or from about 9% to about 10%, (w/w) of the enzyme formulation.

Use of the Formulations of the Present Invention

In use, the enzyme formulation of the present invention may be used for preventing or treating a digestive disorder. The digestive disorder may include, as non-limiting examples dyspepsia, abdominal pain, lactose intolerance, gastric reflux, inflammatory bowel disease and constipation. According to an embodiment, the dyspepsia may comprise common symptoms such as bloating, belching, nausea, and heartburn.

According to another embodiment, the present invention includes a method for preventing or treating a digestive disorder comprising administering to a subject in need thereof an effective amount of a composition of the present invention. Non limiting examples of digestive disorder include dyspepsia, abdominal pain, lactose intolerance, gastric reflux, inflammatory bowel disease, and constipation.

Non-limiting examples of symptoms associated with dyspepsia comprises bloating, belching, nausea, and heartburn.

According to another embodiment, the formulation of the present invention may be used following ingestion of foods of questionable freshness, or stomach flu.

The subject may be any animal have a digestive system. Preferably, the subject is a human.

The present invention will be more readily understood by referring to the following examples which are given to illustrate the invention rather than to limit its scope.

EXAMPLE 1

Enzyme Formulation No. 81

TABLE 1

Active Ingredient Percentages for enzyme formulation (by weight)

| Active Ingredient | Active Ingredients Only (by weight) % | Cumulative % | Total Ingredients (Active plus Inactive) % | Cumulative % |
| --- | --- | --- | --- | --- |
| Protease 6.0 | 10.0 | 10.0 | 6.0 | 6.0 |
| Invertase | 5.0 | 15.0 | 3.0 | 9.0 |
| Glucoamylase | 6.0 | 21.0 | 3.6 | 12.6 |
| Protease 4.5 | 13.0 | 34.0 | 7.8 | 20.4 |
| Protease 3.0 | 9.0 | 43.0 | 5.4 | 25.8 |
| Lipase | 12.0 | 55.0 | 7.2 | 33.0 |
| Lactase | 7.0 | 62.0 | 4.2 | 37.2 |
| Cellulase | 9.0 | 71.0 | 5.4 | 42.6 |
| Catalase | 9.0 | 80.0 | 5.4 | 48.0 |
| Alpha-galactosidase | 12.0 | 92.0 | 7.2 | 55.2 |
| Alpha-amylase | 5.0 | 97.0 | 3.0 | 58.2 |
| Pectinase | 3.0 | 100.0 | 1.8 | 60.0 |
| S/T | 100.0 | | 60.0 | |

TABLE 2

Active and Inactive Ingredient Percentages per capsule (by weight)

| | % of Total Formula | Cumulative % |
| --- | --- | --- |
| Active Ingredients | 60.0 | 60.0 |
| Inactive Ingredients | 40.0 | 100.0 |
| S/T | 100.0 | |

TABLE 3

Inactive Ingredient Percentages per Capsule (by weight)

| Inactive Ingredient | % of Total Formula | Cumulative % |
| --- | --- | --- |
| Rice Bran | 38.0 | 38.0 |
| Silica | 1.5 | 39.5 |
| Maltodextrin | 0.5 | 40.0 |
| S/T | 40.0 | |

EXAMPLE 2

Enzyme Formulation No. 2

TABLE 4

Active Ingredient Percentages for enzyme formulation (by weight)

| Active Ingredients | % active ingredients | Cumulative % |
| --- | --- | --- |
| Protease 6.0 | 17.39 | 17.39 |
| Invertase | 15.94 | 33.33 |
| Glucoamylase | 14.17 | 47.5 |
| Protease 4.5 | 13.04 | 60.54 |
| Protease 3.0 | 12.87 | 73.41 |
| Lipase | 9.42 | 82.83 |
| Lactase | 7.25 | 90.08 |
| Cellulase | 4.54 | 94.62 |
| Catalase | 2.9 | 97.52 |
| Bromelain | 1.9 | 99.42 |
| Alpha-galactosidase | 0.58 | 100 |

TABLE 5

Active and Inactive Ingredient Percentages per capsule (by weight)

| | % of Total Formula | Cumulative % |
| --- | --- | --- |
| Active Ingredients | 31.54 | 31.54 |
| Inactive Ingredients | 68.46 | 100.0 |
| S/T | 100.0 | |

TABLE 6

Inactive Ingredient Percentages per Capsule (by weight)

| Inactive Ingredient | % of Total Formula | Cumulative % |
| --- | --- | --- |
| Rice Bran | 68.23 | 68.23 |
| Silica | 0.25 | 68.46 |
| S/T | 68.46 | |

EXAMPLE 3

Test of the Enzyme Formulations

Four subjects having histories of digestive disorders were provided with formulation No. 2 for use as necessary. One or two tables of the formulation 2 are recommended before, during or after a meal, as necessary.

Subject 1, female, describes a history of severe heartburn and reflux associated with GERD. The symptoms developed in the last trimester of her first pregnancy 21 years ago, and have been plaguing her since then. Since then, subject 1 has had recurring digestive distress, including feelings of having her stomach "scraped". Subject 1 has been treated with different medications including Ranitidine and Nexium, with mixed results, including important side effects such as massive headaches, constipation and sometimes a jittery, shaky feeling. Subject 1 ingested the enzyme formulation for a few months, and all the digestive disorders symptoms have disappeared and have not recurred since then. No side effects have been observed. Subject 1 ingests a dose when eating rich, fatty food or spicy food as a preventive measure.

Subject 2, female, describes light use of the formulation of the present invention mostly in circumstances when having an upset stomach, after consumption of larger than usual quantities of milk products causing her abdominal pain and bloating, or meat products causing her constipation. Subject 2 also use the formulation of the present invention when feeling nauseated following ingesting of a food product which may have gone bad, and/or experiencing the symptoms of stomach flu. In such circumstances, subject 2 described relief of the discomfort experienced during these conditions.

Subject 3, female, describe a history of digestive disorders including bloating, gas and indigestion, coupled with constipation. Subject 3 takes the formulation of the present invention with every meal, and her digestion and elimination process has been greatly improved.

Subject 4, female, describe a history of digestive disorders after ingesting cereal products containing wheat, and dairy products. This includes bloating, gas and indigestion, coupled with constipation. Subject 4 takes the formulation of the present invention when consuming prepared meals, or meals at restaurant or friend's house, where she does not have complete control over the ingredients. She report that her digestion and elimination process has been greatly improved.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. An enzyme formulation consisting of:
   about 9% (wt/wt) of protease 3.0,
   about 13% (wt/wt) of protease 4.5,
   about 10% (wt/wt) of protease 6.0,
   about 5% (wt/wt) of invertase,
   about 6% (wt/wt) of glucoamylase,
   about 7% (wt/wt) of lactase,
   about 9% (wt/wt) of cellulase,
   about 12% (wt/wt) of alpha-galactosidase,
   about 5% (wt/wt) of alpha-amylase,
   about 3% (wt/wt) of pectinase,
   about 9% to 10% (wt/wt) catalase, and
   about 12% to 15% (wt/wt) lipase,
   in combination with an acceptable pharmaceutical carrier.

2. The enzyme formulation of claim 1, wherein said invertase, said glucoamylase, said lactase, said cellulase, said alpha-galactosidase, said pectinase, said catalase and said alpha-amylase are all of fungal origin.

3. A food supplement comprising an enzyme formulation of claim 1.

4. A method for preventing or treating a digestive disorder comprising administering to a subject in need thereof an effective amount of the enzyme formulation of claim 1.

5. The method of claim 4, wherein said digestive disorder comprises dyspepsia, abdominal pain, lactose intolerance, gastric reflux, inflammatory bowel disease, and constipation.

6. The method of claim 5, wherein said dyspepsia comprises at least one of bloating, belching, nausea, and heartburn.

* * * * *